United States Patent
Oota et al.

(10) Patent No.: US 8,454,823 B2
(45) Date of Patent: Jun. 4, 2013

(54) SAMPLE STIRRING DEVICE, LIQUID CHROMATOGRAPHY DEVICE USING SAME, AND SAMPLE CONTAINER STAND

(75) Inventors: Shin-ichi Oota, Kyoto (JP); Hidenari Yamagata, Kyoto (JP); Takeshi Takagi, Kyoto (JP); Koji Egawa, Kyoto (JP)

(73) Assignee: Arkray, Inc., Kyoto-shi (JP)

( * ) Notice: Subject to any disclaimer, the term of this patent is extended or adjusted under 35 U.S.C. 154(b) by 248 days.

(21) Appl. No.: 13/121,872

(22) PCT Filed: Oct. 2, 2009

(86) PCT No.: PCT/JP2009/067216
§ 371 (c)(1),
(2), (4) Date: Mar. 30, 2011

(87) PCT Pub. No.: WO2010/038852
PCT Pub. Date: Apr. 8, 2010

(65) Prior Publication Data
US 2011/0174708 A1    Jul. 21, 2011

(30) Foreign Application Priority Data
Oct. 3, 2008 (JP) ................................. 2008-258704

(51) Int. Cl.
*B01D 15/08* (2006.01)
(52) U.S. Cl.
USPC ........ 210/198.2; 210/656; 366/208; 366/214; 366/218

(58) Field of Classification Search
USPC ....... 210/635, 656, 101, 198.2, 219; 366/208, 366/214, 218; 494/16, 19
See application file for complete search history.

(56) References Cited

U.S. PATENT DOCUMENTS

| | | | |
|---|---|---|---|
| 5,861,563 | A | 1/1999 | Boyd et al. |
| 6,123,205 | A | 9/2000 | Dumitrescu et al. |
| 6,156,275 | A | 12/2000 | Dumitrescu et al. |
| 2008/0271852 | A1 | 11/2008 | Giacalone |

FOREIGN PATENT DOCUMENTS

| | | | |
|---|---|---|---|
| JP | 07-055815 | * | 3/1995 |
| JP | 7-55815 A | | 3/1995 |
| JP | 10-332709 A | | 12/1998 |
| JP | 11-230969 A | | 8/1999 |
| JP | 2005-321306 A | | 11/2005 |
| JP | 2008-536106 A | | 9/2008 |

OTHER PUBLICATIONS

PTO Translation No. 13-2221 of Japan Patent No. 7-55815.*
PTO Translation No. 13-2220 of Japan Patent No. 2005-321306.*

* cited by examiner

*Primary Examiner* — Ernest G Therkorn
(74) *Attorney, Agent, or Firm* — Fox Rothschild LLP

(57) ABSTRACT

A sample stirring device of the present invention includes a driving roller and two follower rollers for coming into contact with a sample container including a cylindrical portion for containing a sample to be stirred. The driving roller is driven for rotation to stir the sample contained in the sample container. The two follower rollers have rotation axes inclined with respect to an axial direction of the cylindrical portion. This arrangement allows the sample container such as a blood collection tube to be rotated stably.

4 Claims, 17 Drawing Sheets

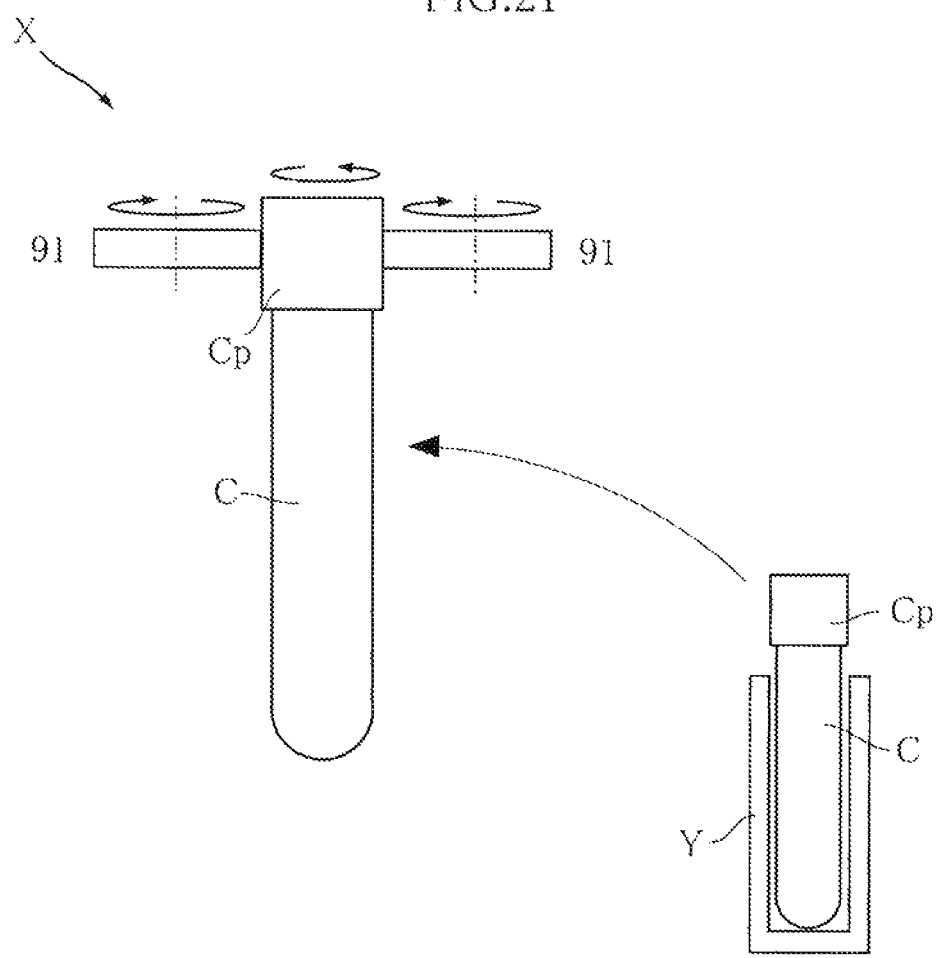

SAMPLE STIRRING DEVICE, LIQUID CHROMATOGRAPHY DEVICE USING SAME, AND SAMPLE CONTAINER STAND

INCORPORATION BY REFERENCE

This application is a 371 of International Application No. PCT/JP2009/067216 filed Oct. 2, 2009, which claims priority to Japanese Patent Application No. 2008-258704 filed Oct. 3, 2008, the entire contents of which being hereby incorporated herein by reference.

TECHNICAL FIELD

The present invention relates to a sample stirring device for stirring a sample such as blood, contained in a sample container such as a blood collection tube. The invention also relates to a liquid chromatography device using such a sample stirring device, and a sample container stand for holding the sample container.

BACKGROUND ART

In recent years, liquid chromatography is often used as a sample analysis method in the field of organic chemistry, biochemistry and medicine. In e.g. a blood test using such a liquid chromatography device, blood collected in a cylindrical blood collection tube is used as a sample. However, blood, if left as it is, separates into blood plasma and blood cells, which leads to incorrect test results. Thus, some liquid chromatography devices are provided with a sample stirring device for stirring blood collected in a blood collection tube. FIG. 21 shows an example of conventional sample stirring device (see Patent Document 1, for example). The illustrated sample stirring device X includes a plurality of rollers 91. Any one of these rollers 91 is driven by a motor, not shown. A blood collection tube C containing blood is held upright in e.g. a stand Y, with a cap Cp attached to it. The blood collection tube C is set between the rollers 91. When the motor starts driving, the rollers 91 and the blood collection tube C start to rotate. Thus, blood in the blood collection tube C is stirred. After the stirring, e.g. a needle-like nozzle (now shown) breaks through the cap Cp to dip the end of the nozzle in the blood. The blood is drawn up through the nozzle and tested as a sample by the liquid chromatography device.

With this arrangement, however, in performing stirring with respect to the blood collection tube C, the blood collection tube C may move in the axial direction relative to the rollers 91. Conceivably, this is because the side surface of the blood collection tube C is not necessarily perpendicular to the rollers 91, which are held horizontally. For instance, when the blood collection tube C is slightly tapered with the dimension in cross section gradually reducing toward the end, the blood collection tube C tends to move upward. Further, a bar-code label for identification is usually attached to the blood collection tube C. When the rollers 91 rotate in contact with the bar-code label or the bar-code label comes into contact with a structural part of the sample stirring device X during rotation, the bar-code label may peel off, which may cause a further problem of hindrance of proper rotation of the blood collection tube C.

The blood collection tube C is held upright in a rack Y, for example. For holding the blood collection tube C upright in the rack Y, some portions of the rack Y need to be in contact with the blood collection tube C. For stable holding of the blood collection tube C, it is desirable that the rack comes into contact with an upper portion of the blood collection tube C. However, the bar-code label for identification is usually attached to an upper portion of the blood collection tube C, so that the bar-code label may be damaged or peeled by the rack Y.

Patent Document 1: JP-A-H07-55815

DISCLOSURE OF THE INVENTION

Problems to be Solved by the Invention

The present invention has been proposed under the circumstances described above. It is therefore an object of the present invention to provide a sample stirring device that allows stable rotation of a sample container such as a blood collection tube, a liquid chromatography device using such a stirring device, and a sample container stand that allows stable holding of a sample container such as a blood collection tube in an upright posture.

Means for Solving the Problem

According to a first aspect of the present invention, there is provided a sample stirring device comprising one or more rollers adapted to come into contact with a sample container including a cylindrical portion for containing a sample to be stirred. At least one of the rollers is configured to be driven for rotation to stir the sample contained in the sample container, and at least one of the rollers has a rotation axis inclined with respect to an axial direction of the cylindrical portion.

In a preferred embodiment of the present invention, the rollers are three rollers spaced apart from each other in the circumferential direction of the cylindrical portion.

In a preferred embodiment of the present invention, one of the three rollers is a rotation driving roller having a rotation axis extending in the axial direction of the cylindrical portion, whereas other two of the rollers are follower rollers having rotation axes inclined toward a same side with respect to the axial direction of the cylindrical portion.

In a preferred embodiment of the present invention, the sample stirring device comprises a sample container moving mode for moving the sample container toward a first side in the axial direction by rotating the one or more rollers in a first direction; and a sample stirring mode for stirring the sample, by rotating the one or more rollers in a second direction reverse to the first direction, with a supporter for preventing the sample container from moving toward a second side opposite from the first side in the axial direction being arranged on the second side of the sample container.

In a preferred embodiment of the present invention, the supporter includes an inclined surface that extends toward the first side in the axial direction as proceeding away from the sample container in a radial direction of the cylindrical portion. In the sample container moving mode, the inclined surface is arranged on the second side of the sample container in the axial direction.

In a preferred embodiment of the present invention, in the sample container moving mode, the one or more rollers are rotated alternately in the first direction and in the second direction.

In a preferred embodiment of the present invention, the supporter includes a holding surface provided farther from the sample container in the radial direction of the cylindrical portion than the inclined surface is, and arranged on the second side of the sample container in the axial direction in the sample stirring mode.

According to a second aspect of the present invention, there is provided a liquid chromatography device comprising the sample stirring device provided according to the first aspect of the present invention.

According to a third aspect of the present invention, there is provided a sample container stand for holding a sample container, which includes a cylindrical portion for containing a sample, in an upright posture. The sample container stand comprises three or more contact portions for coming into contact with the cylindrical portion. At least one of the contact portions is different from others in a position in the circumferential direction of the cylindrical portion and in the axial direction of the cylindrical portion.

In a preferred embodiment of the present invention, the contact portions are configured to come into contact with a point within a lower half portion of a height of the sample container.

In a preferred embodiment of the present invention, the sample container stand comprises a first contact portion for coming into contact with the cylindrical portion; a pair of second contact portions positioned on an opposite side of the first contact portion across a first plane, the first plane being perpendicular to a diameter of the cylindrical portion that passes through the first contact portion and containing a center axis of the cylindrical portion, the second contact portions being spaced apart from each other across a second plane perpendicular to the first plane and containing the center axis, the second contact portions being arranged to come into contact with the cylindrical portion on one side, in the axial direction, of a third plane, the third plane being perpendicular to the first and the second planes and passing through the first contact portion; and a pair of third contact portions that are positioned on an opposite side of the first contact portion across the first plane, spaced apart from each other across the second plane, and arranged to come into contact with the cylindrical portion on the other side; in the axial direction, of the third plane.

In a preferred embodiment of the present invention, the paired second contact portions are at a same position in the axial direction, and the paired third contact portions are at a same position in the axial direction.

In a preferred embodiment of the present invention, each of the second contact portions and one of the third contact portions that is on a same side as the second contact portion with respect to the second plane are at a same position in the circumferential direction of the cylindrical portion.

In a preferred embodiment of the present invention, the sample container stand further comprises an elastic biasing portion capable of applying an elastic force to the cylindrical portion in a direction toward the center of the cylindrical portion, and the first contact portion is provided at the elastic biasing portion.

In a preferred embodiment of the present invention, the sample container stand further comprises a pair of tongue portions positioned on an opposite side of the elastic biasing portion across the first plane, spaced apart from each other across the second plane, and extending in the axial direction. Each of the second contact portions is provided at a root of a respective one of the tongue portions, and each of the third contact portions is provided at an end of a respective one of the tongue portions.

Other features and advantages of the present invention will become more apparent from the detailed description given below with reference to the accompanying drawings.

BRIEF DESCRIPTION OF THE DRAWINGS

FIG. 21 is a side view showing a conventional sample stirring device.

BEST MODE FOR CARRYING OUT THE INVENTION

Preferred embodiments of the present invention are described below with reference to the accompanying drawings.

Figure 1:
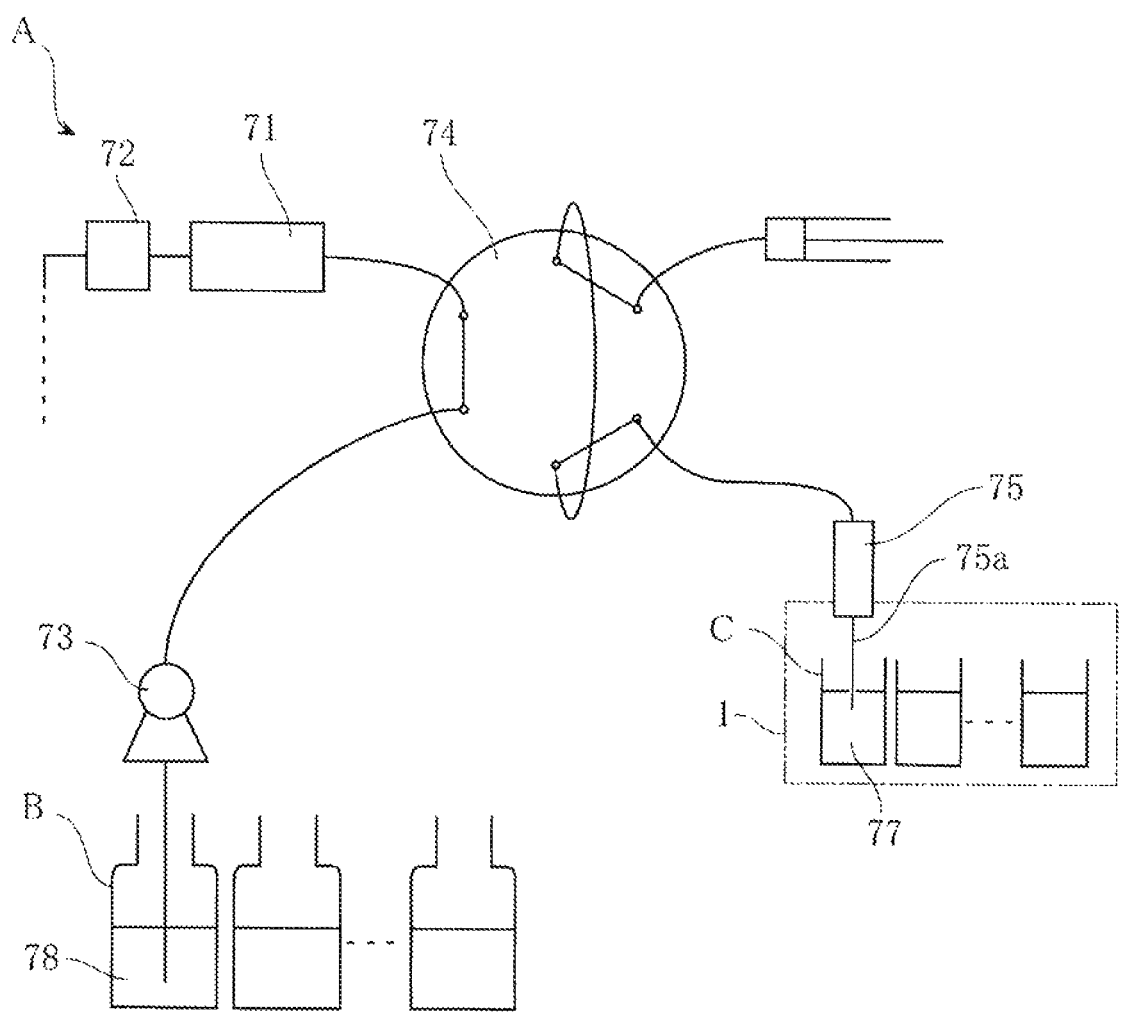
FIG. 1 is a system structural view showing an example of a liquid chromatography device according to the present invention.

FIG. 1 shows an example of liquid chromatography device according to the present invention. The liquid chromatography device A of this embodiment includes a column 71, a detector 72, a liquid feed pump 73, an injection valve 74, a feeder 75 and a sample stirring device 1. The liquid chromatography device A separates blood 77, which is a sample, into components for analysis by using an eluant 78, which is a mobile phase.

The column 71 contains filler for adsorbing blood 77 introduced into the column. After the blood 77 is adsorbed to the filler, the eluant 78 is introduced into the column 71, whereby the adsorbed blood 77 is desorbed by the eluant 78. The desorbed blood 77 and the eluant 78 flow through the column 71 as an effluent and are then discharged.

The detector 72 performs measurement of absorbance with respect to the effluent flowing through the column 71 to analyze the components of the blood 77.

The liquid feed pump 73 is attachable to a mobile phase container B storing the eluant 78 to feed the eluant 78 from the mobile phase container B to the column 71. The liquid feed pump 73 is also used to feed blood 77 within the injection valve 74 to the column 71.

The injection valve 74 comprises e.g. a six-way valve and is rotatable. In order for the liquid feed pump 73 to feed the eluant 78 to the column 71, the injection valve is connected as illustrated in the figure. In order to feed the blood 77 to the column 71, the injection valve is connected in an orientation rotated e.g. 60 degrees from the illustrated state.

The feeder 75 serves to feed the blood 77 from a blood collection tube C, in which blood 77 is stored, to the injection valve 74, and is provided with a nozzle 75a. The nozzle 75a can draw up the blood 77 when inserted in the blood collection tube C.

Figure 2:
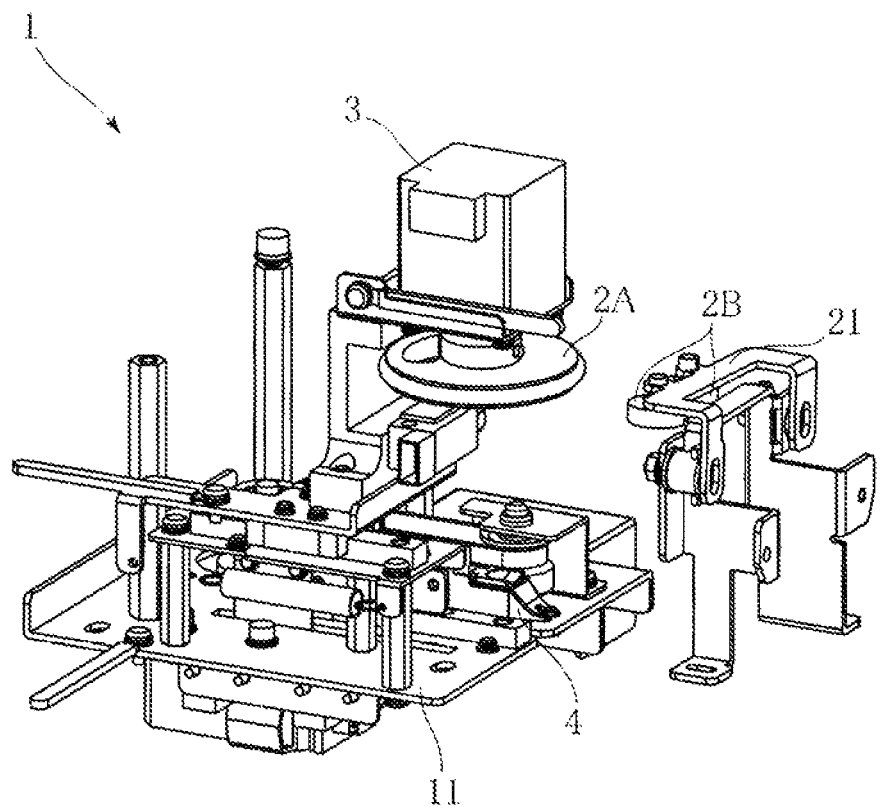
FIG. 2 is a perspective view showing an example of a sample stirring device according to the present invention.

The sample stirring device 1 is a device for stirring the blood 77 in the blood collection tube C before the blood 77 is drawn up with the nozzle 75a. As shown in FIG. 2, the sample stirring device 1 includes a driving roller 2A, two follower rollers 2B, a motor 3, a bracket 21, a stage 11 and a supporter 4.

The driving roller 2A, the motor 3, the support 4 and so on are mounted on the stage 11. The stage is capable of moving the driving roller 2A, the motor 3 and the supporter 4 in a horizontal direction toward and away from the two follower rollers 2B. The driving roller 2A has a vertical rotation axis and is driven by the motor 3. The periphery of the driving roller 2A is made of e.g. synthetic rubber. In this embodiment, the driving roller 2A has a relatively large diameter. The motor 3 is e.g. a DC motor and serves as the driver for the driving roller 2A.

Figure 3:
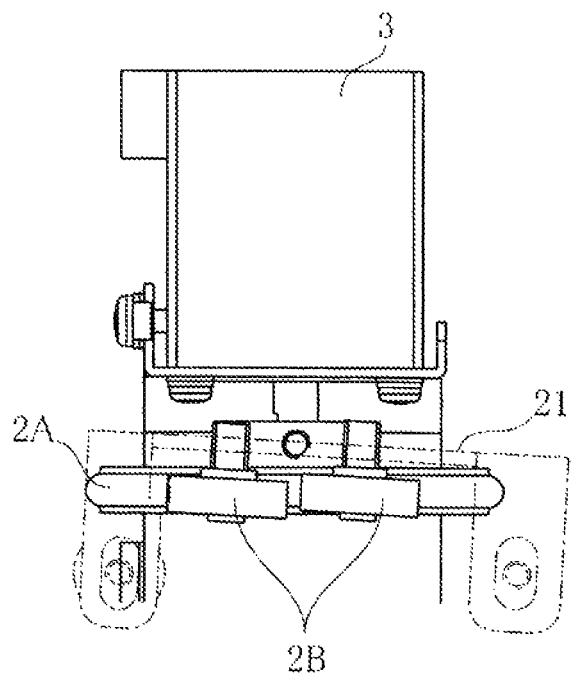
FIG. 3 is a front view showing a principal portion of the sample stirring device of FIG. 2.
Figure 4:
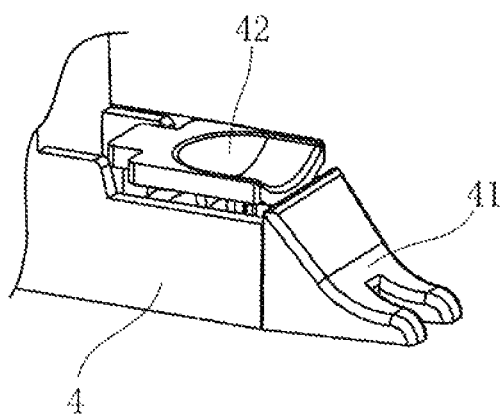
FIG. 4 is an enlarged perspective view showing a principal portion of a supporter of the sample stirring device of FIG. 2.
Figure 5:
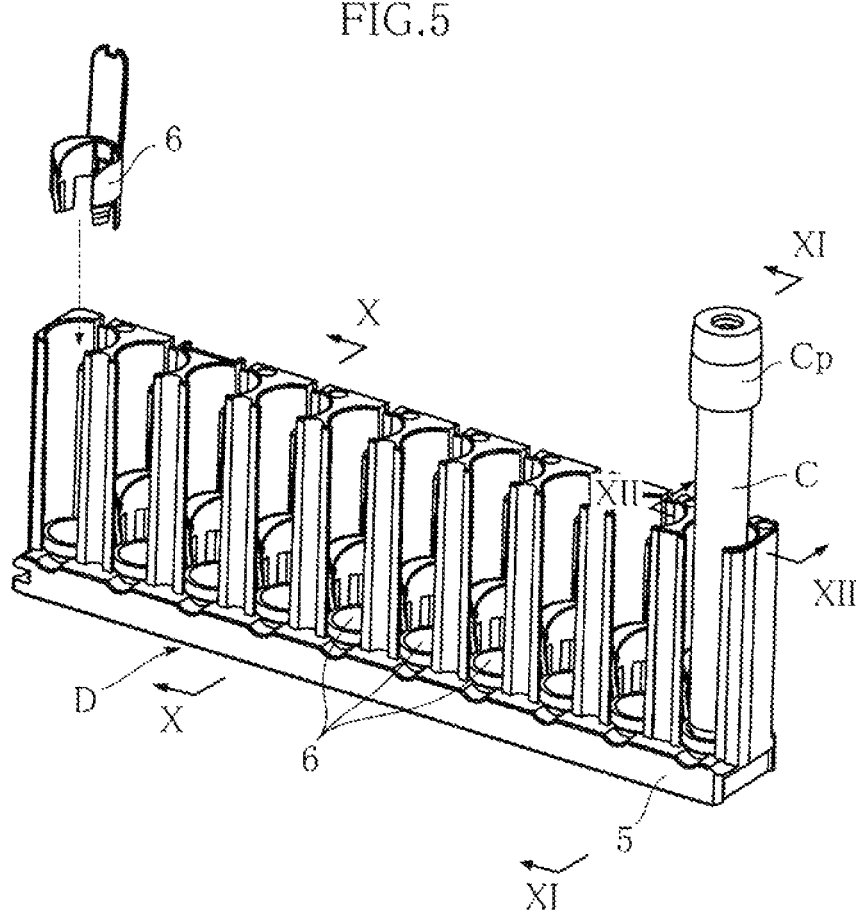
FIG. 5 is a partially-exploded perspective view showing an example of a blood collection tube stand according to the present invention.

The two follower rollers 2B are non-driven rollers that are not connected to a driver such as a motor, and spaced apart from the driving roller 2A in the horizontal direction. The two follower rollers 2B are rotatably supported by the bracket 21. FIG. 3 is a side view showing a principal portion of the sample stirring device 1 as viewed from the two follower rollers 2B side. In this figure, the illustration of the stage 11, the supporter 4 and so on is omitted. As shown in the figure, the bracket 21 is inclined upward from right to left in the figure with respect to the horizontal. Since the bracket 21 is inclined in this way, the two follower rollers 2B are also inclined upward from right to left with respect to the horizontal. A spacer (not shown) is provided between the bracket 21 and the two follower rollers 2B to hold the two follower rollers 2B at the same position in the vertical direction. In this embodiment, the two follower rollers 2B are smaller in diameter than the driving roller 2A.

The supporter 4 is provided to support the blood collection tube C from below, and includes an inclined surface 41 and a holding surface 42. The inclined surface 41 is inclined to be positioned higher in the vertical direction as proceeding away from the two rollers 2B in the horizontal direction. The holding surface 42 is positioned farther from the two rollers 2B than the inclined surface 41 is and comprises a concave surface similar to a reversed spherical surface. The supporter 4 is movable relative to the stage 11 toward and away from the two follower rollers 2B.

FIGS. 5 and 10-12 show an example of sample container stand according to the present invention. The blood collection tube stand D of this embodiment is used in stirring the blood 77 in the blood collection tube C by the sample stirring device 1 or drawing up the blood 77 with the nozzle 75a. The blood collection tube stand D comprises a case 5 and a plurality of adapters 6 and is capable of holding a plurality of blood collection tube C in a row, each in an upright posture. Each adapter 6 is incorporated in the case 5 at a position adjacent to a lower end of a space for receiving a blood collection tube C. As shown in FIGS. 6-9, the adapter 6 is made of e.g. ABS resin and includes an elastic biasing portion 61, a projection 61a, a pair of arms 62, a pair of projections 62a, a pair of tongues 63, a pair of tongue ends 63a and a pair of slits 64.

The elastic biasing portion 61 extends downward, and as shown in FIGS. 8-11, is slightly inclined so that its end is positioned closer to the center of the mounted blood collection tube C. When the blood collection tube C is mounted, the elastic biasing portion 61 is elastically bent outward in the radial direction of the blood collection tube C, and as a reaction to this, the elastic biasing portion 61 applies an elastic force onto the blood collection tube C. The projection 61a is provided at the end of the elastic biasing portion 61 and an example of a first contact portion of the present invention.

Figure 6:
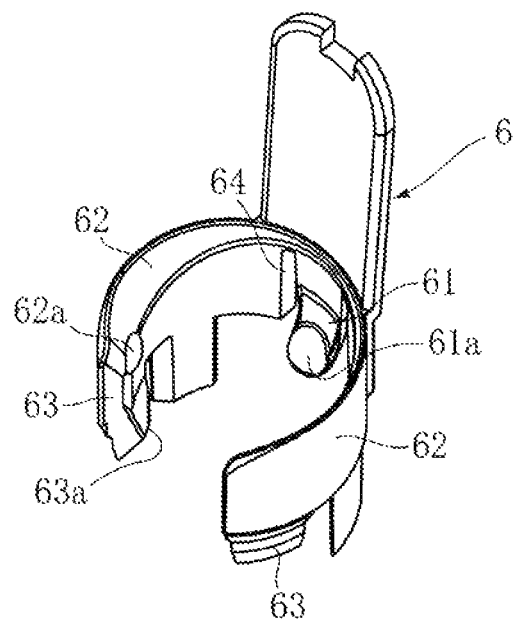
FIG. 6 is a perspective view showing an adapter used for the blood collection tube stand of FIG. 5.
Figure 7:
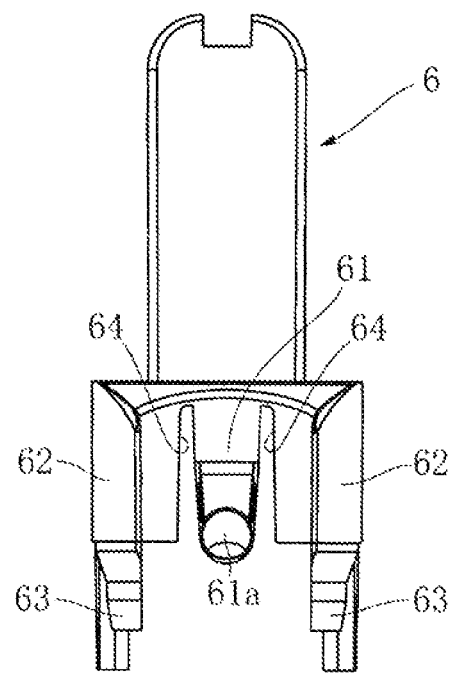
FIG. 7 is a front view showing the adapter used for the blood collection tube stand of FIG. 5.
Figure 8:
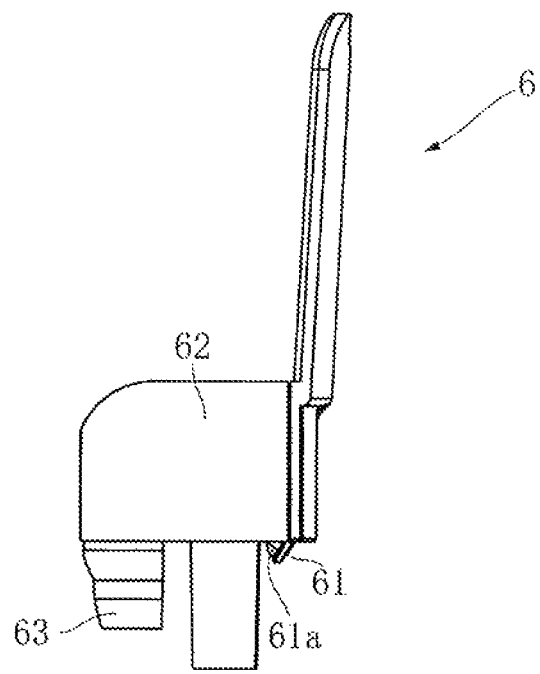
FIG. 8 is a side view showing the adapter used for the blood collection tube stand of FIG. 5.
Figure 9:
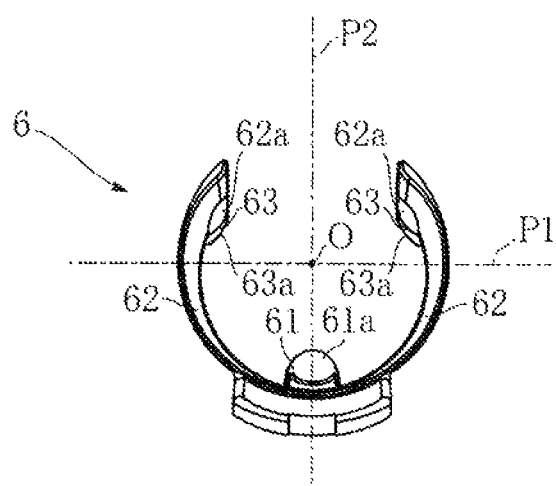
FIG. 9 is a plan view showing the adapter used for the blood collection tube stand of FIG. 5.

As shown in FIGS. 6 and 9, the paired arms 62 extend from the elastic biasing portion 61 in opposite directions along the circumference of the blood collection tube C. Each of the arms 62 has an end at which the tongue 63 is formed to extend downward. Each tongue 63 has a root at which the projection 62a is formed. Each tongue 63 is further formed with the tongue end 63, which has a relatively sharp shape. The paired projections 62a are an example of a pair of second contact portions of the present invention. The paired tongue ends 63a are an example of a paired third contact portions of the present invention.

As shown in FIG. 9, the paired projections 62a and the paired tongue ends 63a are on the opposite side of the projection 61a across a plane P1. Herein, the plane P1 is a plane that is perpendicular to the diameter passing through the projection 61a, among the diameters of the cylindrical portion of the blood collection tube C mounted on the blood collection tube stand D, and that contains the center axis O of the cylindrical portion. The paired projections 62a are opposite to each other across a plane P2. Herein, the plane P2 is a plane that is perpendicular to the plane P1 and that contains the center axis O. Similarly, the paired tongue ends 63a are opposite to each other across the plane P2. Moreover, in this embodiment, one of the projections 62a and one of the tongue ends 63a are provided at the same position in the circumferential direction of the cylindrical portion, while the other one of the projections 62a and the other one of the tongue ends 63a are provided at the same position in the circumferential direction of the cylindrical portion. In the circumferential direction of the cylindrical portion, the projection 61a and each of the projections 62a or each of the tongue ends 63a are spaced approximately 120 degrees apart from each other.

Figure 10:
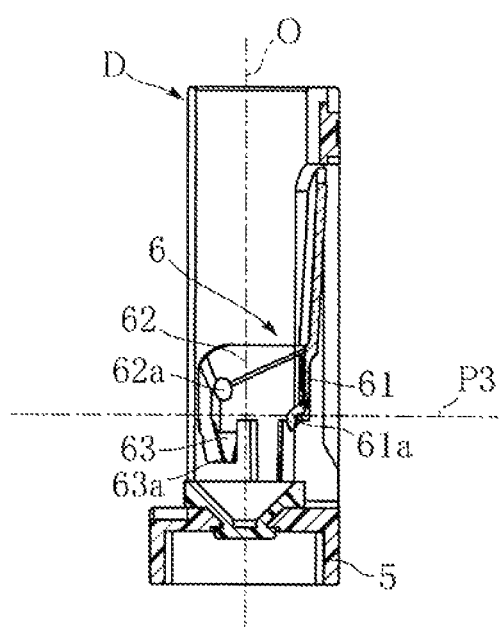
FIG. 10 is a sectional view taken along lines X-X in FIG. 5.

The paired projections 62a are provided at the same position in the vertical direction and positioned above a plane P3 (see FIG. 10). Herein, the plane P3 is a plane that is perpendicular to both of the planes P1 and P2 and that passes through the projection 61a. The paired tongue ends 63a are provided at the same position in the vertical direction and positioned below the plane P3.

Figure 11:
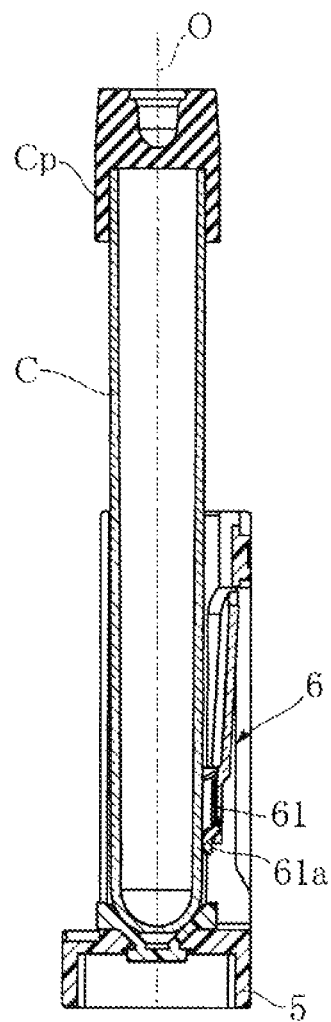
FIG. 11 is a sectional view taken along lines XI-XI in FIG. 5.
Figure 12:
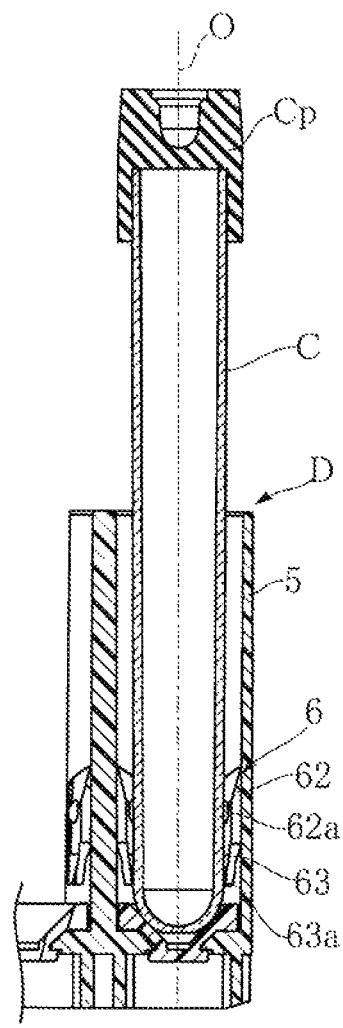
FIG. 12 is a sectional view taken along lines XII-XII in FIG. 5.

As shown in FIGS. 11 and 12, when the blood collection tube C is mounted on the blood collection tube stand D, the projection 61a, paired projections 62a, and paired tongue ends 63a come into contact with the cylindrical portion of the blood collection tube C at five points in total. Other portions of the blood collection tube stand D do not come into contact with the blood collection tube C. Thus, the blood collection tube C is held upright, with its lower portion held in contact with the adapter 6.

The operation of the sample stirring device 1 is described below with reference to FIGS. 13-19.

Figure 13:
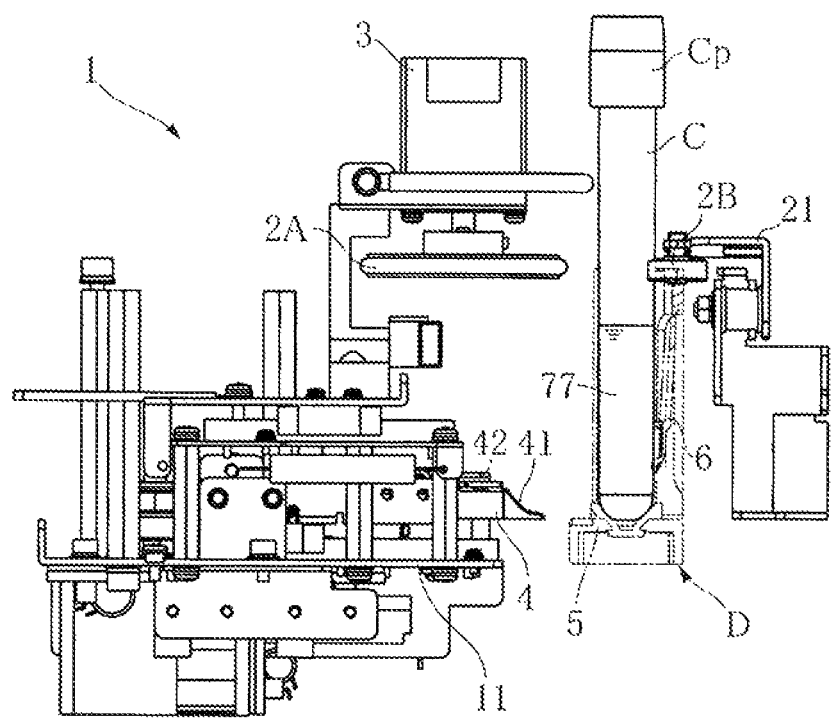
FIG. 13 is a side view showing the state where the blood collection tube stand shown in FIG. 5 is fed to the sample stirring device shown in FIG. 2.
Figure 14:
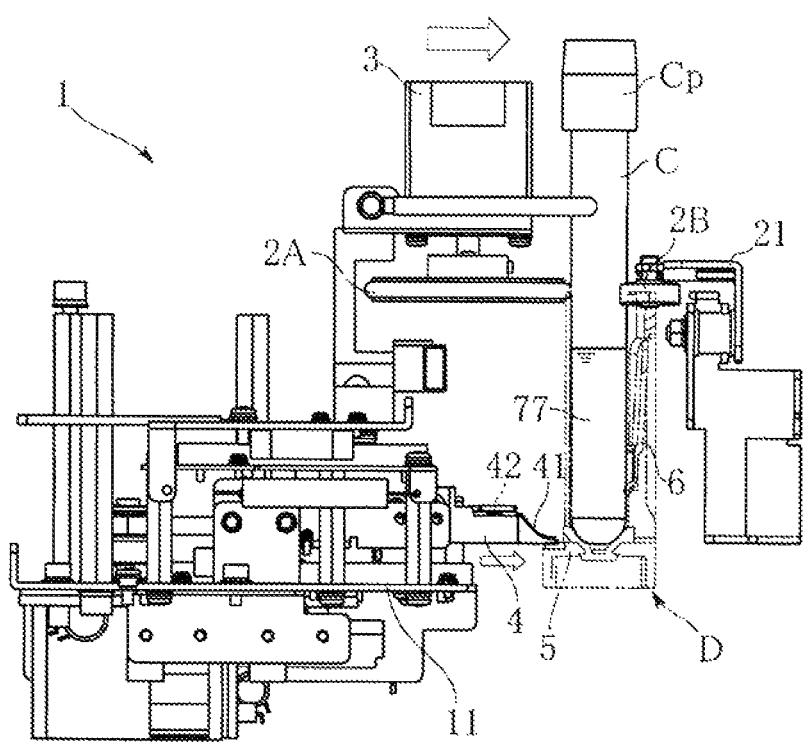
FIG. 14 is a side view showing the sample stirring device of FIG. 2 in the state where a driving roller is pressed against a blood collection tube.

First, as shown in FIG. 13, the blood collection tube stand D, with the blood collection tube C mounted on it, is transferred between the driving roller 2*a* and the two follower rollers 2B. Then, as shown in FIG. 14, the driving roller 2A and the motor 3 move along with the supporter 4 toward the blood collection tube C. By this movement, the blood collection tube C is sandwiched between the driving roller 2A and the two follower rollers 2B. In this state, the supporter 4 is positioned at an approximately equal height to the lower end of the blood collection tube C but spaced apart from the blood collection tube C to the left.

Figure 15:
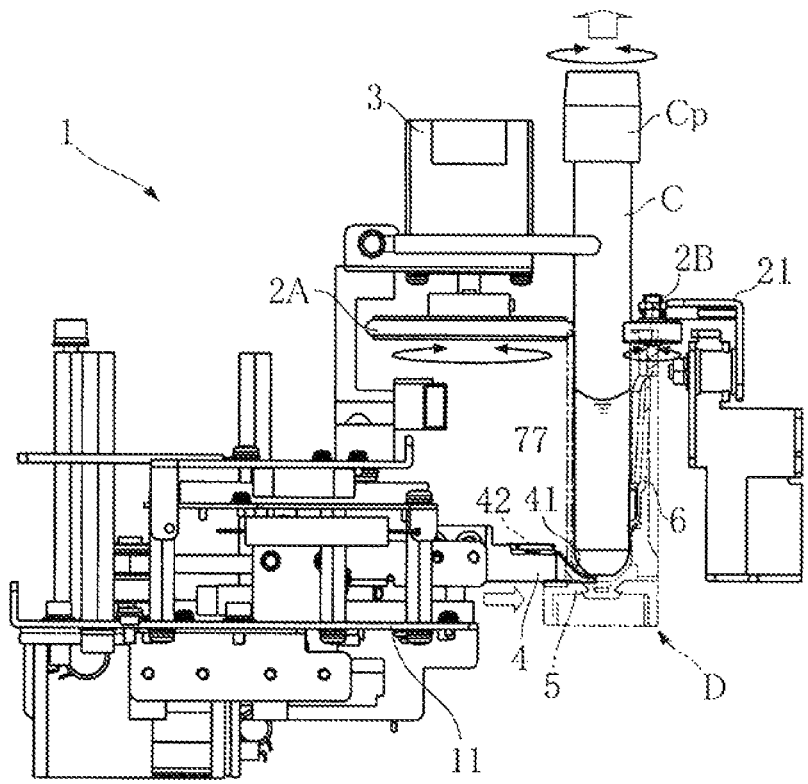
FIG. 15 is a side view showing the sample stirring device of FIG. 2 in a sample container moving mode.
Figure 16:
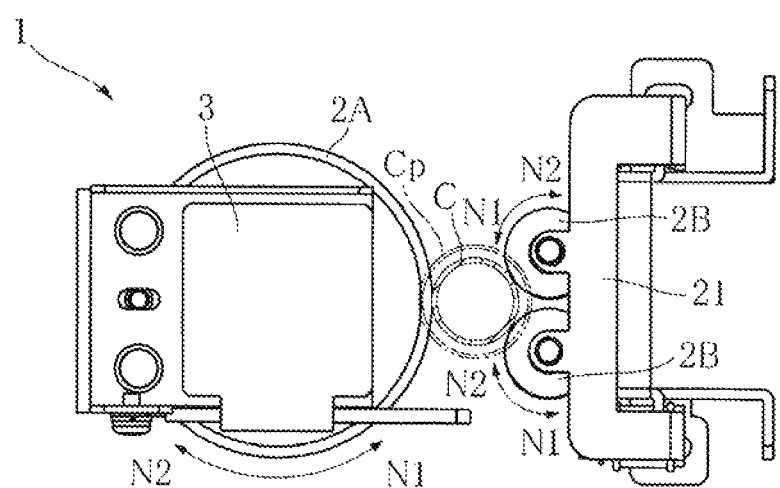
FIG. 16, is a plan view showing a principal portion of the sample stirring device of FIG. 2 in the sample container moving mode.

Then, as shown in FIGS. 15 and 16, the driving roller 2A starts to rotate. By this, the device enters the sample container moving mode of the present invention. Specifically, in this mode, the driving roller 2A quickly alternates forward rotation in direction N1 and reverse rotation in direction N2. Thus, the blood collection tube C and the two follower rollers 2B quickly alternate forward rotation and reverse rotation.

The two follower rollers 2B are inclined in the direction shown in FIG. 3. Thus, when the two follower rollers 2B rotate forward in direction N1, the follower rollers 2B act in such a manner as to swing up the blood collection tube C to the upper left. Thus, when the driving roller 2A and the two follower rollers 2B rotate forward, the blood collection tube C receives a force for moving the tube upward. Conversely, when the driving roller 2A and the two follower rollers 2B rotate in reverse in direction N2, the blood collection tube C receives a force for moving the tube downward.

Figure 17:
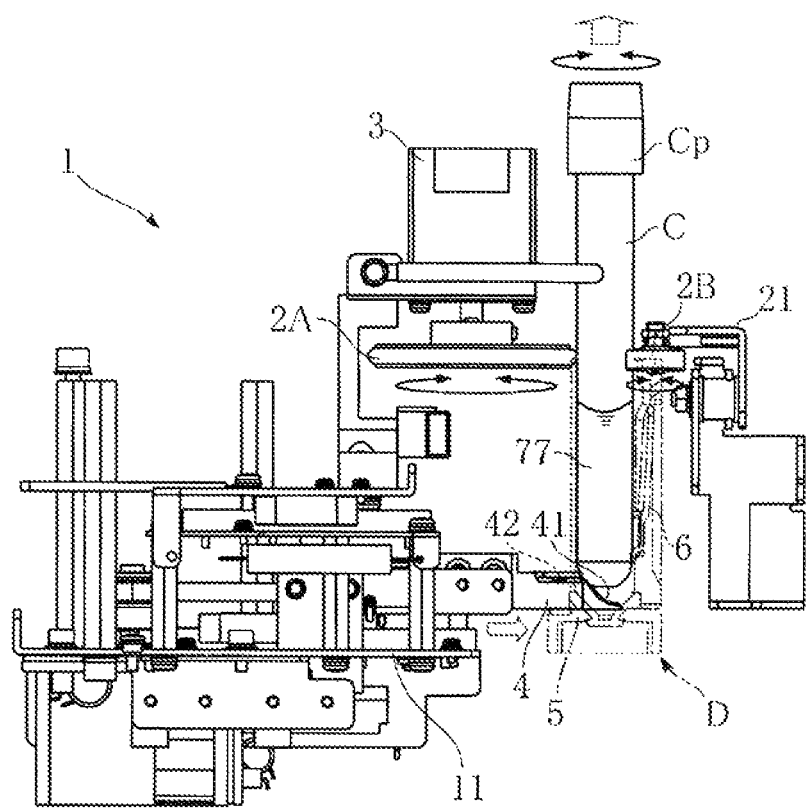
FIG. 17 is a side view showing the sample stirring device of FIG. 2 in the sample container moving mode.
Figure 18:
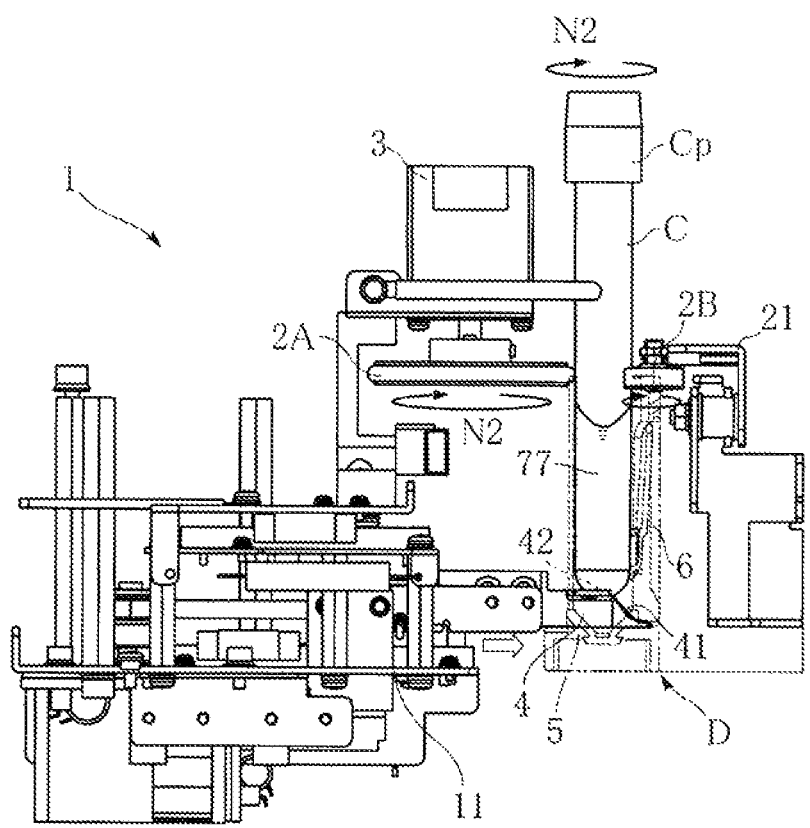
FIG. 18 is a side view showing the sample stirring device of FIG. 2 in a sample stirring mode.

In the sample container moving mode, as shown in FIG. 15, the supporter 4 moves forward to the right so that the leading end of the inclined surface 41 is positioned under the blood collection tube C. With this arrangement, when the driving roller 2A and the two follower rollers 2B rotate forward, the blood collection tube C moves upward, and when the driving roller 2A and the two follower rollers 2B rotate in reverse, the inclined surface 41 of the supporter 4 keeps the blood collection tube C from moving downward, though the blood collection tube receives a downward force. The supporter 4 gradually moves forward in accordance with the forward rotation and reverse rotation of the driving roller 2A and the two follower rollers 2B. Thus, as shown in FIG. 17, the blood collection tube C repeats the upward movement during the sample container moving mode.

When the blood collection tube C reaches a predetermined height, the sample stirring device 1 enters a sample stirring mode. Herein, the "predetermined height" is e.g. the height where the bar-code label for identification, attached to a relatively upper portion of the blood collection tube C, is positioned sufficiently higher than the projections 61*a*, 62*a* and the tongue ends 63*a* of the adapter 6, which are the contact portions. In the sample stirring mode, the supporter 4 moves further forward so that the holding surface 42 is positioned directly under the blood collection tube C, as shown n FIG. 18. In this mode, the driving roller 2A and the two follower rollers 2B continuously perform only reverse rotation in direction N2. Thus, the blood collection tube C constantly receives a downward force. However, the blood collection tube C is kept from moving downward, due to the presence of the holding surface 42 of the supporter 4. Thus, the blood collection tube C is continuously rotated at the predetermined height. By this rotation, the blood 77 in the blood collection tube C is stirred vigorously.

Figure 19:
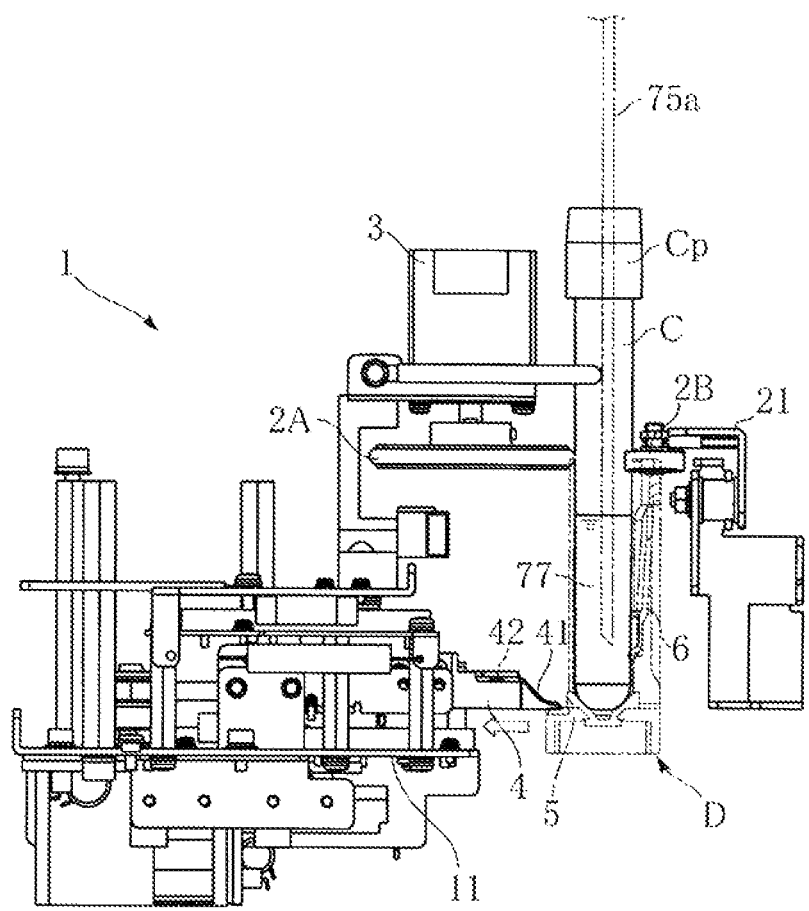
FIG. 19 is a side view showing the drawing up of blood after the sample stirring mode in the sample stirring device of FIG. 2.

After the sample stirring mode is finished, the driving roller 2A stops. Then, as shown in FIG. 19, the supporter 4 moves away from the blood collection tube C to the left, and with the blood collection tube C still sandwiched between the driving roller 2A and the two follower rollers 2B, the nozzle 75*a* is inserted into the blood 77 by breaking through the cap Cp. The blood 77 is drawn up with the nozzle 75*a*. Thereafter, the above-described liquid chromatography is performed.

The advantages of the sample stirring device 1, liquid chromatography device A and blood collection tube stand D are described below.

According to this embodiment, the blood 77 is stirred by the sample stirring mode after the blood collection tube C is moved by the sample container moving mode to a height suitable for the stirring. Thus, in the sample stirring mode in which the blood collection tube C is rotated at a relatively high speed, the bar-code label or the like attached to the blood collection tube C is prevented from peeling off.

The inclined arrangement of the two follower rollers 2B allows a force for moving the blood collection tube C upward to be applied during the forward rotation and a force for moving the blood collection tube C downward to be applied during the reverse rotation. This prevents the blood collection tube C from moving in an unintentional direction during the rotation of the driving roller 2A and the two follower rollers 2B.

In the sample container moving mode, the bar-code label may be still positioned at a height where the bar-code label can come into contact with the projections 61*a*, 62*a* and the tongue ends 63*a* of the adapter 6, which are the contact points. In this state, if the blood collection tube C is rotated continuously in one direction, the bar-code label may peel off from its edge. In this embodiment, however, the driving roller 2A quickly alternates forward rotation and reverse rotation. This contributes to preventing the bar-code label from peeling off in the sample container moving mode.

In the sample container moving mode, the provision of the supporter 4 allows the blood collection tube C to intermittently move upward, without moving downward, in spite of the alternate forward rotation and reverse rotation. In the sample stirring mode, continuous rotation is performed, with the blood collection tube C slightly pressed against the holding surface 42 of the supporter 4. This allows the blood 77 to be stirred, with the blood collection tube C held stably.

The blood 77 is sufficiently stirred in the sample stirring mode, and hence, it is unlikely that blood plasma and blood cells are undesirably separated in the blood after the sample stirring mode. Thus, the liquid chromatography using the blood 77 drawn up with the nozzle 75*a* provides correct analysis results.

The blood collection tube stand D of this embodiment holds the blood collection tube C upright at five points in total, i.e., at the projection 61*a*, the paired projections 62*a* and the paired tongue ends 63*a*. This holding is achieved by arranging the projection 61*a* and each of the projections 62*a* or each of the tongue ends 63*a* to be spaced apart from each other in the circumferential direction and arranging the paired projections 62*a* and the paired tongue ends 63*a* to be opposite from each other in the vertical direction across the projection 61*a*. This allows the adapter 6 for holding the blood collection tube C to be arranged adjacent to the lower end of the blood collection tube C. This ensures that the bar-code label, which is often attached to a relatively upper portion of the blood collection tube C, is prevented from peeling off, while the blood collection tube C is stably held upright.

The projections 62*a* and the tongue ends 63*a* are aligned in the circumferential direction and in the vertical direction. This is suitable for ensuring stable holding of the blood collection tube C. Moreover, the elastic force applied by the elastic biasing portion 61 allows the blood collection tube C to be held reliably in contact with the projection 61*a*, the paired projections 62*a* and the paired tongue ends 63*a*. The tongue ends 63*a* can properly fit to the blood collection tube C even if the diameter is changed to some degree.

Figure 20:
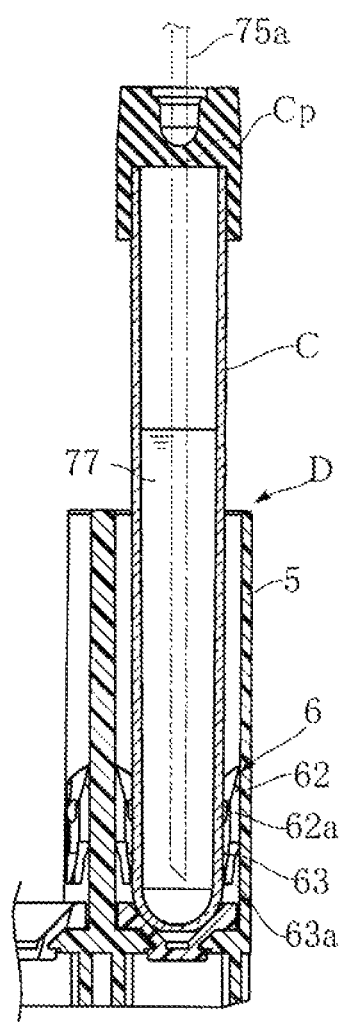
FIG. 20 is a sectional view showing the drawing up of blood from a blood collection tube mounted on a blood collection tube stand according to the present invention.

The blood collection tube stand D may not be used in combination with the sample stirring device 1 but used only for drawing up the blood 77. As shown in FIG. 20, in a test which does not particularly require the stirring of the blood 77, blood 77 can be drawn up with the nozzle 75*a* from the blood collection tube C held upright. In this case again, since the blood collection tube C is stably held upright, the blood 77 is properly drawn up.

The sample stirring device 1, the liquid chromatography device and the blood collection tube stand of the present invention are not limited to the foregoing embodiment. Each part of the sample stirring device, the liquid chromatography device and the blood collection tube stand can be varied in design in many ways.

The number of the driving roller 2A and follower rollers 2B are not limited to the number described in the foregoing embodiment. Instead of the follower rollers 2B, the driving roller 2A may be arranged in an inclined posture. Although performing alternate forward rotation and reverse rotation in the sample container moving mode is preferable for preventing the bar-code label from peeling off, the present invention is not limited to this, and only forward rotation may be performed in the sample container moving mode. The sample to be stirred by the sample stirring device according to the present invention is not limited to blood but may be any liquid which needs to be stirred for avoiding separation or the like. Although the sample stirring device is suitable for incorporation in a liquid chromatography device, the application of the sample stirring device is not limited to this.

The first through the third contact portions of the present invention are not limited to those having the above-described configuration, but may be configured otherwise as long as they can achieve point contact. Instead of employing the adapter 6 having the first through the third contact portions, the case 5 integrally formed with the adapter 6 may be employed. The sample container of the present invention is not limited to the blood collection tube C and may be any sample container that can contain liquid. The contact portions of the present invention may be any three portions that can come into contact with the cylindrical portion, and arranging these contact portions at different positions in the circumferential direction and the axial direction of the cylindrical portion provide the advantage of stably holding the sample container in an upright posture.

The invention claimed is:

1. A sample stirring device comprising:
three rollers adapted to come into contact with a sample container including a cylindrical portion for containing a sample to be stirred, the three rollers being spaced apart from each other in a circumferential direction of the cylindrical portion, wherein:
one of the three rollers is a rotation driving roller having a rotation axis extending in the axial direction of the cylindrical portion, and the other two of the three rollers are follower rollers having rotation axes inclined toward a same side with respect to the axial direction of the cylindrical portion;
the rotation driving roller is configured to be driven for rotation to stir the sample contained in the sample container, and
the follower rollers have a rotation axis inclined with respect to an axial direction of the cylindrical portion;
the sample stirring device comprising:
a sample container moving mode for moving the sample container toward a first side in the axial direction by rotating the rotation driving roller in a first direction; and
a sample stirring mode for stirring the sample, by rotating the rotation driving roller in a second direction reverse to the first direction, with a supporter for preventing the sample container from moving toward a second side opposite from the first side in the axial direction being arranged on the second side of the sample container.

2. The sample stirring device according to claim 1, wherein: the supporter includes an inclined surface that extends toward the first side in the axial direction as proceeding away from the sample container in a radial direction of the cylindrical portion; and
in the sample container moving mode, the inclined surface is arranged on the second side of the sample container in the axial direction.

3. The sample stirring device according to claim 2, wherein, in the sample container moving mode, the rotation driving roller is rotated alternately in the first direction and in the second direction.

4. The sample stirring device according to claim 2, wherein the supporter includes a holding surface provided farther from the sample container in the radial direction of the cylindrical portion than the inclined surface is, the holding surface being arranged on the second side of the sample container in the axial direction in the sample stirring mode.

* * * * *